United States Patent [19]

Takaki et al.

[11] Patent Number: 4,908,472

[45] Date of Patent: Mar. 13, 1990

[54] PREPARATION PROCESS OF CINNAMATE ESTER

[75] Inventors: Usaji Takaki; Shinobu Aoki; Yoshihiro Yamamoto; Isao Hara, all of Kanagawa, Japan

[73] Assignee: Mitsui Toatsu Chemicals, Inc., Tokyo, Japan

[21] Appl. No.: 291,207

[22] Filed: Dec. 28, 1988

[30] Foreign Application Priority Data

Dec. 28, 1987 [JP] Japan .................. 62-330164

[51] Int. Cl.$^4$ ............................................. C07C 69/76
[52] U.S. Cl. ..................................... 560/104
[58] Field of Search ...................... 560/109

[56] References Cited

U.S. PATENT DOCUMENTS

| 3,530,168 | 9/1970 | Biale et al. | 560/104 |
| 4,620,027 | 10/1986 | Hsu | 560/104 |
| 4,656,306 | 4/1987 | Takaki | 560/104 |
| 4,661,620 | 4/1987 | Takaki | 560/104 |

FOREIGN PATENT DOCUMENTS

| 0097935 | 5/1985 | Japan . |
| 0109545 | 6/1985 | Japan . |
| 0169441 | 9/1985 | Japan . |
| 0231630 | 10/1985 | Japan . |
| 0237046 | 10/1985 | Japan . |
| 2123152 | 6/1987 | Japan . |

*Primary Examiner*—Paul L. Killos
*Attorney, Agent, or Firm*—Burns, Doane, Swecker & Mathis

[57] ABSTRACT

The invention relates to a process for preparing a cinnamate ester comprising forming a reaction mixture of a styrene compound, an alcohol and a catalyst in a reactor; blowing a feed gas mixture of carbon monoxide, oxygen and an inert gas into the reaction mixture through at least one feed port; collecting a discharge gas flowing from the reactor and passing the gas through a condenser to form a condensate; recirculating the condensate into the reactor; blowing into the reaction mixture through at least one feed port other than the feed port(s) for the feed gas mixture, a gas selected from the groups consisting of the discharge gas and an inert gas; and isolating the cinnamate ester from the mixture.

16 Claims, 1 Drawing Sheet

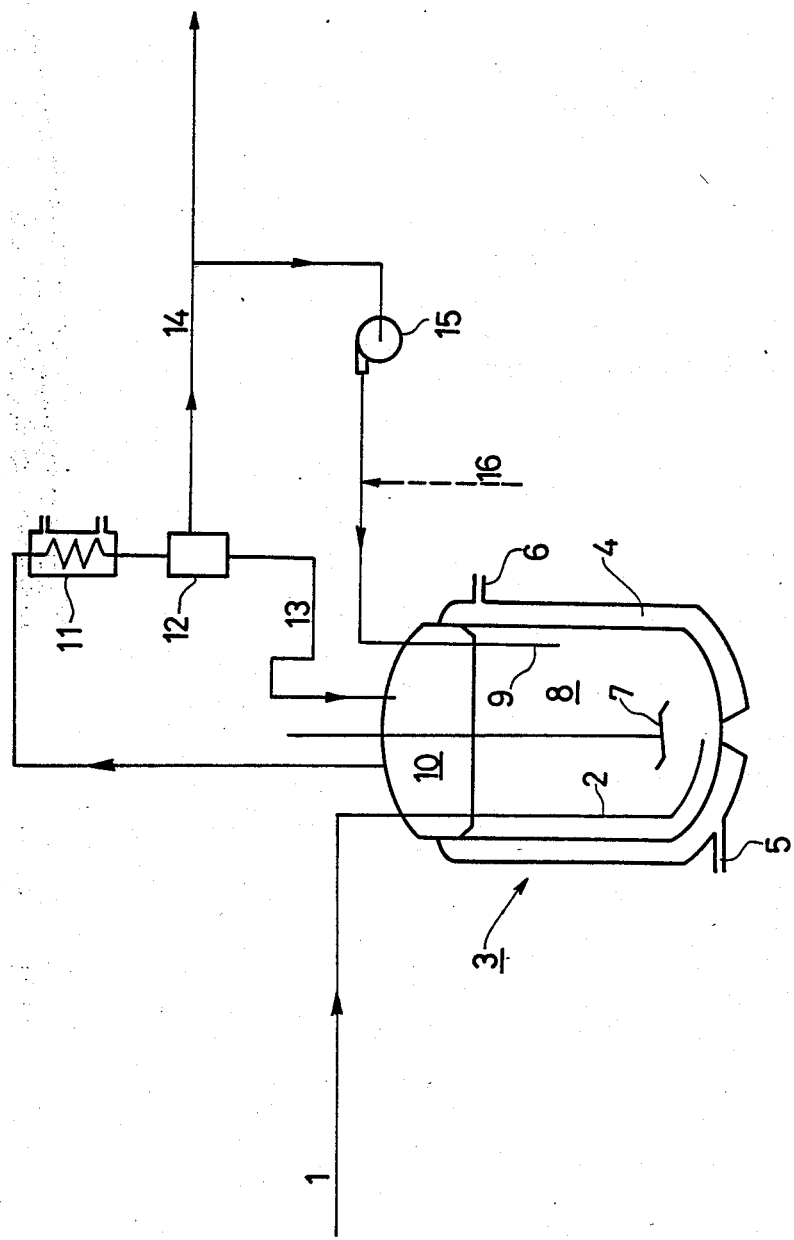

PREPARATION PROCESS OF CINNAMATE ESTER

BACKGROUND OF THE INVENTION

(1) Field of the Invention

The present invention relates to a process for preparing a cinnamate ester. The process comprises reacting a styrene compound having a structure that corresponds to the structure of the cinnamate ester to be prepared with an alcohol, carbon monoxide and oxygen in the presence of a catalyst. The heat evolved during the reaction is readily removed from the reactor, thus providing an economical and industrially practical process for preparing a cinnamate ester.

(2) Description of the Related Art

Cinnamate esters are useful as perfume bases and as starting materials therefor. They are also important as starting materials for agricultural chemicals, photosensitive resins and in the synthesis of the amino acid phenylalanine.

Cinnamic acid has conventionally been produced by a process in which benzaldehyde and an acetic acid derivative are used as the principal starting materials. However, such starting materials are expensive and thus, the cinnamic acid produced is also expensive. Accordingly, such a process is not economical for use on an industrial scale.

A process for making a cinnamate ester from less expensive starting materials has been proposed wherein a styrene compound is reacted with carbon monoxide, an alcohol compound and oxygen in the presence of a catalyst. (See Japanese Patent Application Laid-Open Nos. 15242/1981; 70836/1982, 92242/1985 and 77352/1987 and U.S. Pat. No. 4,661,620). However, the proposed reaction is oxidative and releases a large amount of heat. Thus, for industrial use, an effective method for removing the heat is needed. Prior art reactions for preparing a cinnamate ester relate to only small scale production. The prior art does not suggest an effective method for removing the large heat of reaction produced when the process is practiced on an industrial scale.

In a general reaction, it is routine to use a jacket cooler provided outside a reactor or a cooling tube disposed in a reaction mixture to remove heat evolved in the reactor. However, such methods are limited to reactions practiced on a small scale or to reactions of an extremely small heat release value. Where a large amount of heat is evolved in the present reaction (for example, the heat of reaction from styrene to methyl cinnamate is about 81 kcal/mole) use of the above routine methods fails to provide a sufficient heat transfer area commensurate with the exotherm rate for practicing the process on an industrial scale. Thus, none of these methods can be used industrially as the principal method for removing the heat of reaction. However, such methods may be used as auxiliary heat removal methods.

One skilled in the art may contemplate circulating the reaction mixture through an external heat exchanger. However, such method poses the problem that complex facilities are required, as well as additional energy to circulate a large amount of liquid.

On the other hand, another method for removing heat uses the heat of evaporation of a liquid component in a reactor. However, the method is generally employed under conditions wherein a solvent boils, and thus is not effective when a reaction is carried out below the boiling point of the solvent.

SUMMARY OF THE INVENTION

The present invention overcomes the problems and disadvantages of the prior art by providing a process for preparing a cinnamate ester wherein the heat evolved during the reaction of a corresponding styrene compound, an alcohol, carbon monoxide and oxygen is simply and effectively removed from the reactor, even on an industrial scale, without impairing the reaction results and catalytic activity.

The present invention provides a process for preparing a cinnamate ester by reacting a corresponding styrene, an alcohol, carbon monoxide, and oxygen in the presence of a catalyst preferably comprising (1) at least one palladium metal or a compound thereof and (2) at least one copper compound.

The reaction is carried out by blowing a feed gas mixture containing carbon monoxide, oxygen and an inert gas into a reaction mixture containing a corresponding styrene, alcohol and a catalyst in a reactor. A discharge gas flowing out from the reactor containing vapor formed by the evaporation of the liquid components in the reactor is passed through a condenser. The resulting condensate is recirculated back into the reactor while the remaining gas is discharged. A gas selected from a portion of the discharged gas, or an inert gas such as nitrogen, argon or carbon dioxide provided separately, is blown into the reaction mixture through a feed port different than the port through which the feed gas mixture was introduced to increase the evaporation rates of the liquid components in the reactor, whereby heat evolved inside the reactor is removed.

The accompanying drawing, which is incorporated in and constitutes a part of this specification, illustrates an embodiment of the invention and together with the description, serves to explain the principles of the invention.

BRIEF DESCRIPTION OF THE DRAWING

FIG. 1 is a flow chart showing a reactor employed in the Examples.

DETAILED DESCRIPTION OF THE INVENTION

Reference will now be made in detail to the present preferred embodiments of the invention, an example of which is illustrated in the accompanying drawing.

Exemplary styrene compounds suitable for use in the practice of this invention include styrene; alkyl derivatives of styrene such as α-methylstyrene, β-methylstyrene, α-ethylstyrene, β-ethylstyrene, o-methylstyrene, m-methylstyrene, p-methylstyrene, m-ethylstyrene, p-ethylstyrene, p-tertbutylstyrene and p-isopropyl-β-methylstyrene, and styrene derivatives that contain one or more substituents on the aromatic ring which do not impair the reaction, such as p-chlorostyrene, p-methoxystyrene and 3,4-dimethoxystyrene.

Exemplary suitable alcohols for use in the process of the invention include aliphatic alcohols such as methanol, ethanol, propanol, butanol, pentanol, octanol, cyclopentanol and cyclohexanol. The alcohol compounds may contain one or more substituents that do not impair the reaction, such as halogen atoms and alkoxy groups. The alcohol may be used in an amount of from about 0.5 to about 100 moles of alcohol per mole of styrene compound. The alcohol may be used both as a starting material and as a reaction solvent. One or more additional solvents may also be employed, providing that such solvents do not impair the reaction.

Any catalysts can be used providing that they can convert a styrene compound, an alcohol, carbon monoxide and oxygen to a corresponding cinnamate ester. Preferably, a catalyst containing at least one palladium metal or a compound thereof and at least one copper compound is used.

Exemplary suitable palladium metals or compounds thereof for use as the first component of the catalyst in the process of the invention include palladium black; a palladium metal carried on a carrier such as activated carbon, silica gel, alumina, silica alumina, magnesia, zeolite or a molecular sieve; an O-valent palladium complex such as palladium benzylideneacetone complex or tetrakis(triphenylphosphine) palladium; or a divalent palladium compound, for example, an inorganic acid salt of palladium such as palladium chloride or palladium nitrate; an organic acid salt of palladium such as palladium acetate or palladium benzoate, or a palladium complex such as bis(acetylacetonate) palladium, cyclooctadienedichloropalladium, palladium chloride benzonitrile complex, palladium chloride pyridine complex or palladium chloride amine complex. These palladium metals and palladium compounds may be used either singly or in combination.

The palladium metals or compounds thereof may be used in an amount of about 0.1 gram atom per mole of styrene or less, preferably from about $5 \times 10^{-6}$ to about $1 \times 10^{-2}$ gram atom per mole of styrene.

Exemplary suitable copper compounds for use as the second component of the catalyst in the process of the invention include copper halide compounds such as copper chloride or copper bromide; an inorganic acid salt of copper such as copper carbonate or copper nitrate; an organic acid salt of copper such as copper acetate, copper propionate, copper stearate, copper cinnamate or copper benzoate; a copper complex compound such as copper acetyl acetonate or copper benzoyl acetonate. The copper compounds may be used either singly or in combination. The copper compound employed is preferably soluble in the reaction mixture, however, the process of the invention will not be impaired if a portion of the copper compound remains undissolved. The copper compound may be used in an amount of from about 0.004 to about 0.4 gram atom per liter of reaction mixture, preferably from about 0.008 to about 0.3 gram atom per liter of reaction mixture.

In the process of the invention, various additional compounds may be added to improve the catalytic activities, reaction results or to achieve additional desired purposes. Illustrative suitable compounds include (1) compounds of alkali metals, alkaline earth metals and aluminum-group metals; (2) compounds of metals selected from Group 4A, Group 5A, Group 7A, Group 8A (iron-group) and Group 2B of the periodic table; (3) compounds of rare earth elements; (4) halogen compounds; (5) inorganic and organic acids such as nitric acid and acetic acid; (6) tertiary amine compounds; (7) nitriles; (8) dehydrating agents; and (9) phenols and quinones. The compounds may be used either singly or in combination. Some of these compounds are disclosed in U.S. Pat. No. 4,661,620, which disclosure is incorporated herein by reference.

In the process of the invention, carbon monoxide and oxygen are employed as gaseous starting materials. These gases will hereafter be referred to collectively as the "feed gas."

In order to avoid the range of explosion, the feed gases are preferably used as a mixture with an inert gas such as nitrogen, argon or carbon dioxide. Air may be used as an oxygen source. It is preferable to use carbon dioxide in combination with the feed gas since the presence of carbon dioxide in the reaction system can improve the reaction results. More than two inert gases may be used at the same time. A gaseous mixture containing at least the feed gas and inert gas, which are to be fed for the reaction will hereafter be referred to as a "feed gas mixture". The feed gas is usually fed as a single feed gas mixture for the reaction after mixing the feed gas with inert gas and the like. In some instances, the feed gas mixture may be used by dividing it into two or more gas mixtures of different compositions. Although the feed gas mixture may always be prepared from fresh gases, a gas which has been taken out of the reaction system subsequent to its use in the reaction may be fed, as the feed gas mixture for the next reaction, after adjusting its composition as needed. This may be repeated. The feed gas mixture is fed by blowing it into the reaction mixture. Its feeding may be effected through a single port or through plural ports. A spreader or diffuser may be employed to enhance the spreading of the gas whenever needed.

In the process of this invention, the concentration of the feed gas in the feed gas mixture, which is required to avoid the potential danger of explosion and to obtain satisfactory reaction results, is dependent on the kind of inert gas and reaction conditions and thus cannot be specified. Preferably, the concentrations of carbon monoxide, and oxygen in the feed gas mixture are from about 3 to about 30 vol. % carbon monoxide and from about 1.5 to about 25 vol. % oxygen. More preferably, the concentrations are from about 5 to about 20 vol. % carbon monoxide and from about 3 to about 18 vol. % oxygen.

The molar ratio of carbon monoxide to oxygen in the feed gas mixture is from about 0.5 to about 3.0. The reaction results or catalytic activities are reduced if the molar ratio of carbon monoxide to oxygen in the feed gas mixture falls below 0.5 or exceeds 3.0. Preferably, the molar ratio ranges from about 0.8 to about 2.2.

The molar ratio of carbon monoxide to styrene is from about 0.5 to about 5. The molar ratio varies with the amount of oxygen contained in the feed gas. If the molar ratio of carbon monoxide to styrene is less than 0.5, a large amount of unreacted styrene is present which prevents the reaction from proceeding efficiently. On the other hand, if the molar ratio is greater than 5, a greater amount of the feed gas is consumed to form carbon dioxide through a direct reaction of carbon monoxide and oxygen than for the formation of the cinnamate ester, and thus the economy of the reaction is compromised. Preferably, the molar ratio of carbon monoxide to styrene is from about 1.0 to about 4 moles of carbon monoxide per mole of starting styrene. The molar ratio of oxygen to styrene depends on the molar ratio of carbon monoxide to styrene and carbon monoxide to oxygen.

The amounts of the individual feed gases to be used relative to the styrene can be expressed in terms of products of the concentrations of the respective feed gases in the mixture and the feed rate (flow rate) of the feed gas mixture per unit time. Since the concentrations and amount of components of the feed gas are limited as described above, the flow rate of the feed gas mixture is also limited and hence cannot be freely changed.

The partial pressure of carbon monoxide in the reaction should not be higher than about 50 atm (abs. atm.; hereinafter atm will mean abs. atm.), preferably, from about 0.005 to about 40 atm. The partial pressure of oxygen should not be higher than about 50 atm, preferably, from about 0.002 to about 30 atm. The overall pressure of the reaction should not be higher than about 500 atm, preferably from about 1 to about 300 atm.

The reaction temperature ranges from about room temperature to about 200° C., preferably from about 40° C. to about 160° C.

No particular limitation is imposed on the reaction time, which will vary depending on the reaction conditions. However, the reaction time may generally be carried out in from about 0.01 to about 24 hours, preferably, from about 0.05 to about 10 hours.

Under conditions described above, the feed gas mixture is blown into the reaction mixture. The gaseous mixture which has flowed out of the reactor is a mixed gas composed at least of carbon monoxide and oxygen remaining unconsumed in the reaction, an inert gas and the like constituting a major portion of the mixed gas, and vapor formed as a result of evaporation of liquid components in the reactor. The flow rate of the gaseous mixture increases as the flow rate of the gas passing through the reaction mixture increases. The concentration of the vapor of each liquid component in the gaseous mixture flowing out of the reactor is governed by the ratio of the vapor pressure of the liquid component, which is determined by the kind of the liquid component, its concentration in the reaction mixture and the temperature, to the overall pressure of the reaction. Accordingly, the flow rate of the vapor, i.e., the rate of evaporation, is the product of the flow rate of the gaseous mixture flowing out of the reactor and the proportion of the vapor of the liquid components. The rate of evaporation is dependent on the flow rate of the gas passing through the reaction mixture. As a consequence, the rate of evaporation increases as the flow rate of the gas increases. When the rate of evaporation is multiplied by the average latent heat of vaporization of the liquid components, an intrinsic value, the product thereof is the removal rate of heat by the evaporation of the liquid components. This removal rate of heat is thus dependent on the flow rate of the gas passing through the reaction mixture. The removal rate of heat also increases as the flow rate of the gas increases. The gas passing through the reaction mixture is nothing but that derived from the feed gas mixture unless other gases are fed. Accordingly, the removal rate of heat depends on the flow rate of the feed gas mixture. As has already been described above, the flow rate of the feed gas is limited and thus the flow rate of the feed gas mixture cannot hence be changed freely to achieve a particular removal rate of heat.

The gaseous mixture, which has flowed out of the reactor, is caused to pass through a condenser. The resultant condensate is returned to the reactor, and the remaining gas is discharged. In order to remove heat from the reaction mixture without deteriorating the reaction results and catalytic activities and while maintaining the flow rate of the feed gas mixture, within the preferable range at least a portion of the thus-discharged gas is recirculated and blown back into the reaction mixture through a feed port different from the feed port used for the feed gas mixture.

Alternatively, an inert gas such as nitrogen, argon or carbon dioxide can be separately blown into the reaction mixture through a different feed port. The different feed port may consist of a single opening or plural openings.

As a result, the flow rate of the gas passing through the reaction mixture in the reactor is increased so that the rate of evaporation of each liquid component is increased. Neither the reaction results nor the catalytic activities are impaired by this practice. The flow rate of the discharged gas which is recirculated, or the separately-provided inert gas or the like, can be selected to achieve a particular removal rate of heat.

It is essential to blow the discharge recirculation gas or the separately-provided inert gas or the like into the reaction mixture through a port different from that for the feed gas mixture. If fed through the same feed port, the gases of the different kinds are mixed in the piping so that the feed gas mixture is unnecessarily diluted or the ratio of carbon monoxide to oxygen in the feed gas mixture is changed, whereby certain deleterious effects may be given to the reaction results and catalytic activities. No substantial effects are expected for the enhancement of the removal rate of heat even if the discharged recirculated gas or the separately-provided inert gas is fed into the vapor phase of the reactor instead of being blown into the reaction mixture. Any improvements in the positional relationship, distance and configurations of the two types of feed ports for the feed gas mixture and the discharged recirculation gas or the separately provided inert gas, including the provision of one or more baffles or the like at either one or both of the feed ports are within the scope of the present invention.

The cinnamate ester can be isolated from the reaction mixture by a conventional method such as distillation.

According to the process of this invention, it is possible to achieve, with extreme ease, effective and economical removal of the internal heat produced in the reactor during the reaction to produce a cinnamate ester. The present invention therefore permits preparation of a cinnamate ester on an industrial scale.

The present invention will be further clarified by the following examples, which are intended to be purely exemplary of the invention.

EXAMPLE 1

In a glass-lined 10-liter reactor 3 equipped with a stirrer 7 as shown in the drawing attached hereto were placed 0.39 g (2.2 millimoles) of palladium chloride, 19.0 g of cupric chloride, 84.7 g of cupric acetate monohydrate and 165 g of manganous acetate tetrahydrate, and about 1,000 g of methanol. 2,292 g (22.0 moles) of styrene were then added thereto. Methanol was added to bring the total amount of methanol to 3,525 g, whereby a reaction mixed liquid 8 was formed, and stirred.

A feed gas mixture comprising carbon monoxide, oxygen and carbon dioxide in a ratio of 12:7:81 by volume, which had been regulated by a gas mixing machine, was continuously blown into the reaction mixed liquid 8 through a line 1 and an introduction pipe 2 having an opening (feed gas inlet orifice) above the bottom of the reactor at a flow rate of 1.36 m$^3$/hr (standard state; the same shall apply hereinafter). The temperature was increased while the pressure in the reactor was maintained at 8.5 atm.

The gas was discharged through a gaseous phase 10 in the reactor, a condenser 11, a gas-liquid separator 12 and an exhaust gas line 14. In this case, by the time the temperature reached 100° C., a portion of the exhaust gas was circularly blown into the reaction mixed liquid at a flow rate of 2.74 m³/hr with the aid of a blower 15 from the branch of the exhaust line 14 through an introduction pipe 9 (exhaust gas circulation orifice) which had an opening at a position 65 cm under the surface of the reaction liquid. The reaction was continued at a reaction temperature of 100° C. under a reaction pressure of 8.5 atm for 6 hours, while the feed gas mixture and the circulation exhaust gas were regulated so as to maintain the above-mentioned flow rates while the liquid condensed in the condenser 11 was separated in the gas-liquid separator 12 and flowed back to the reactor 3 through a condensed liquid circulation line 13.

During this period of time, pressurizing hot water was caused to flow through a jacket 4 of the reactor to maintain the reaction temperature (temperature of the reaction mixed liquid) at 100° C. The temperature of the pressurizing hot water in the jacket 4 was 116° C. at a jacket inlet 5 and 114° C. at a jacket outlet 6 after a reaction time of 0.5 hour had elapsed, though it was perceptibly irregular at an early stage of the reaction. Afterwards, the temperatures of the pressurizing hot water at these positions were slightly changed, and after 6 hours, they were 118° C. at the inlet and 116° C. at the outlet. During the reaction, the temperature at the jacket inlet was always higher than the temperature at the jacket outlet, and these temperatures were always higher than the above-mentioned reaction temperature. Thus, the jacket was a heating side, permitting sufficient removal of heat by evaporation of liquid components in the reactor.

After the reaction, cooling and the release of pressure followed. The thus treated reaction liquid was analyzed by a high-speed liquid chromatograph, and it was confirmed that 1.08 moles of styrene and 18.94 moles of methyl cinnamate were contained therein. The conversion of styrene was 95.1%, the selectivity of methyl cinnamate (yield based on the consumed styrene) was 90.5%, and the yield of methyl cinnamate (yield based on the charged styrene) was 86.1%. The number of moles of cinnamate formed per gram atom of palladium as a catalyst component (hereafter referred to as palladium turnover) was 8,610.

Comparative Example 1

The same procedure as in Example 1 was repeated except that the exhaust gas was not circulated through the reaction mixed liquid. In order to maintain a reaction temperature at 100° C., the temperature of hot water flowing through the jacket was 96° C. at the inlet and 98° C. at the outlet of the jacket after a reaction time of 0.5 hour had elapsed. Afterwards, the temperature of the hot water at the inlet and outlet were slightly changed to 98° C. and 99° C., respectively, after 6 hours. During the reaction, the temperature at the jacket outlet was always higher than the temperature at the jacket inlet, and these temperatures were always lower than the above-mentioned reaction temperature. Thus, the jacket was a cooling side.

As will be apparent from the foregoing, if the exhaust gas is not circulated, the removal of heat generated in the reactor cannot be sufficiently achieved by evaporation of liquid components alone, and thus it is necessary to cool the reactor from the outside.

According to the analysis of the thus treated reaction liquid, the conversion of styrene was 96.2%, the selectivity of methyl cinnamate was 90.1%, the yield of methyl cinnamate was 86.7% and the Pd turnover was 8,670. As indicated by these values, reaction results and catalytic activity were similar to those of Example 1 irrespective of the circulation of the exhaust gas.

EXAMPLE 2

The same procedure as in Example 1 was repeated with the exception that instead of circulating the exhaust gas, carbon dioxide gas was blown into a reaction mixed liquid from the outside through a line 16 and the exhaust gas circulation orifice 9 used in Example 1 at the same flow rate as that of the exhaust gas in Example 1. In order to maintain a reaction temperature at 100° C., the hot water at the inlet and outlet of the jacket were maintained at 114° C. and 112° C., respectively, after 0.5 hour had elapsed. After 6 hours, the temperatures were 166° C. and 114° C., respectively. The temperature in the jacket was about the same as in Example 1, and during this period of time, the jacket always was a heating side.

The conversion of styrene was 93.9%, and the selectivity of methyl cinnamate and the yield of methyl cinnamate were 91.2% and 85.6%, respectively. The Pd turnover was 8,560.

It is noted that by this method, the removal velocity of heat generated in the reactor could be accelerated without impairing the reaction results and catalytic activity.

COMPARATIVE EXAMPLE 2

The same procedure as in Example 1 was repeated with the exception that instead of blowing the circulation exhaust gas into the reaction mixed liquid, the exhaust gas was blown together with the feed gas mixture into the reaction mixed liquid by connecting the exhaust gas circulation line to the feed line 1 at the same flow rates as in Example 1. After 0.5 hour of reaction, the temperature at the inlet and outlet of the jacket were 115° C. and 113+ C., respectively, and after 6 hours, were 116° C. and 114° C., respectively. During this period of time, the jacket was always a heating side. With regard to the results of the reaction, the conversion of styrene was 81.6%, and the selectivity and yield of methyl cinnamate were 86.4% and 70.5%, respectively. The Pd turnover was 7,050. In this example, the heat removal velocity was accelerated, however, the reaction was adversely affected.

COMARATIVE EXAMPLE 3

The reaction was carried out as in Example 1. After 2 hours, temperatures at the inlet and outlet of the jacket were 115° C. and 113° C., respectively. The blowing operation of the circulation exhaust gas into the reaction mixed liquid through the exhaust gas circulation orifice was switched to an operation by which the circulation exhaust gas was returned to the gaseous phase in the reactor. Immediately, the temperature of the reaction mixed liquid began to rapidly rise about 100° C., and was steady at 117° C. As is apparent from above, the circulation of the exhaust gas through the gaseous phase cannot provide any effect of accelerating the heat removal velocity.

What is claimed is:

1. A process for preparing a cinnamate ester comprising
   (1) forming a reaction mixture of a styrene compound, an alcohol and a catalyst in a reactor;

(2) blowing a feed gas mixture of carbon monoxide, oxygen and an inert gas into the reaction mixture through at least one feed port;

(3) collecting a discharge gas flowing from the reactor and passing the gas through a condenser to form a condensate;

(4) recirculating the condensate into the reactor;

(5) blowing into the reaction mixture through at least one feed port other than the feed port(s) used in step (2), a gas selected from the group consisting of the discharge gas and an inert gas; and (6) isolating the cinnamate ester from the mixture.

2. The process of claim 1 wherein in step (2) the inert gas is carbon dioxide.

3. The process of claim 1 wherein in step (5) the gas is the discharge gas.

4. The process of claim 1 wherein in step (5) the gas is an inert gas.

5. The process of claim 4 wherein the inert gas is carbon dioxide.

6. The process of claim 1 wherein the styrene compound is selected from the group consisting of styrene, α-methylstyrene, β-methylstyrene, α-ethylstyrene, β-ethylstyrene, o-methylstyrene, m-methylstyrene, p-methylstyrene, m-ethylstyrene, p-ethylstyrene, p-tert-butylstyrene, p-isopropyl-β-methylstyrene, p-chlorostyrene, p-methoxystyrene and 3,4-dimethoxystyrene.

7. The process of claim 1 wherein the alcohol is selected from the group consisting of methanol, ethanol, propanol, butanol, pentanol, octanol, cyclopentanol and cyclohexanol.

8. The process of claim 1 wherein the alcohol is present in an amount of from about 0.5 moles to about 100 moles of alcohol per mole of styrene.

9. The process of claim 1 wherein the catalyst contains at least one palladium metal or a compound thereof and at least one copper compound.

10. The process of claim 9 wherein the palladium metal or compound thereof is selected from the group consisting of palladium black; a palladium metal carried on a carrier, an O-valent palladium complex, an inorganic acid salt of palladium, an organic acid salt of palladium and a divalent palladium complex.

11. The process of claim 9 wherein the palladium metal or compound thereof is present in an amount no greater than about 0.1 gram atom per mole of styrene.

12. The process of claim 9 wherein the copper compound is selected from the group consisting of a copper halide compound, an inorganic acid salt of copper, an organic acid salt of copper, and a copper complex compound.

13. The process of claim 9 wherein the copper compound is present in an amount of from about 0.004 to about 0.4 gram atom per liter of reaction mixture.

14. The process of claim 1 wherein the volume percent of carbon monoxide is from about 3 to about 30 volume percent.

15. The process of claim 1 wherein the volume percent of oxygen is from about 1.5 to about 25 volume percent.

16. The process of claim 1 wherein the molar ratio of carbon monoxide to styrene is from about 0.5 to about 5 moles.

* * * * *